United States Patent [19]

Ristic et al.

[11] Patent Number: 4,596,707
[45] Date of Patent: Jun. 24, 1986

[54] BABESIA PARASITE ANTIGEN USEFUL IN VACCINE AND DIAGNOSTIC REAGENT

[75] Inventors: Miodrag Ristic, Urbana, Ill.; Carlos Arellano, Mexico City, Mexico

[73] Assignee: University of Illinois Foundation, Urbana, Ill.

[21] Appl. No.: 130,481

[22] Filed: Mar. 31, 1980

Related U.S. Application Data

[63] Continuation-in-part of Ser. No. 34,664, Apr. 30, 1979, abandoned.

[51] Int. Cl.$^4$ .............................................. A61K 39/00
[52] U.S. Cl. ...................................... 424/88; 424/85; 424/93; 424/95; 435/7
[58] Field of Search ................... 424/8, 12, 13, 85, 88, 424/93, 95; 435/7; 436/543, 811

[56] References Cited

PUBLICATIONS

Goodheart, An Introduction to Virology, pp. 101-102.
Kruse et al, Tissue Culture Methods & Applications, 1973, pp. 524-527.
Kalter, Procedures for Routine Lab Diagnosis of Virus & Rickettsial Diseases, pp. 42-44.
Erp, Am. J. Trop. Med. Hyg., vol. 27, 1978, pp. 1061-1064.
Sibinovic, Annals of Trop. Med. & Parasit., vol. 63, 1969, pp. 327-336.
Speer, Z. Parasitenk., vol. 50, 1976, pp. 237-244.
Sibinovic, The J. of Parasitology, vol. 53, Dec. 1967, pp. 1121-1129, and Oct. 1967, pp. 919-923.
Ferris, JAVMA, vol. 153, Dec. 15, 1968, pp. 1888-1896.
Mahoney, Experimental Parsit., vol. 20, 1967, pp. 232-241.
Sibinovic, J. Parsit., vol. 13, 1966, pp. 551-553.
Sibinovic, A. J. Vet. Res., vol. 26, 1965, pp. 147-153.
Mahoney, Exper. Parisit., vol. 20, 1967, pp. 125-129.
Curnow, Nature, vol. 217, Jan. 20, 1968, pp. 267-268.
Goodger, Australian Vet. J., vol. 47, 1971, pp. 251-256.
Mahoney, Exper. Parsit., vol. 32, 1972, pp. 71-85.
Goodger, Int. J. for Parsit., vol. 3, 1973, pp. 387-391.
Curnow, Australian Vet. J., vol. 49, 1973, pp. 279-283.
Thoongsuwan, Annals Trop. Med. Parasit., vol. 67, 1973, pp. 373-385.
Sibinovic, Am. J. Vet. Res., vol.35, 1974, pp. 1045-1052.
Goodger, Int. J. for Parsit., vol. 6, 1976, pp. 213-216.
Todorovic, Tropenmed. Parasit., vol. 29, 1978, pp. 210-214.
Sibinovic, Thesis, U. of Illinois, Urbana, Ill., 1966, "Immunogenic Properties of Purified Antigens Isolated from the Serum of Horses, Dogs, and Rats with Acute Babesiosis".
Sibinovic, Diss. Abs., vol 27, No. 7B, 1966, pp. 2547-2548.
Dimopoullos, Am. J. Vet. Res., vol. 37, Jun. 1976, pp. 693-695.

*Primary Examiner*—Sidney Marantz
*Attorney, Agent, or Firm*—Marshall, O'Toole, Gerstein, Murray & Bicknell

[57] ABSTRACT

Soluble antigen, specific for Babesia parasites, is isolated from growth media of Babesia-infected erythrocytes in cell culture and characterized, inter alia, by its ability to inhibit the capacity of specific Babesia serum antibodies to neutralize infectivity of Babesia merozoites in vitro. Antigen preparations provide immunologically active components useful for vaccination of animals against infection by Babesia parasites and may be employed in the preparation of diagnostic reagents.

10 Claims, 2 Drawing Figures

BABESIA PARASITE ANTIGEN USEFUL IN VACCINE AND DIAGNOSTIC REAGENT

This application is a continuation-in-part of co-pending U.S. application Ser. No. 34,664, filed Apr. 30, 1979, abandoned.

BACKGROUND

The present invention relates generally to materials useful in immunization of animals against infection by protozoan parasites of the genus Babesia (Order Piroplasmida). More specifically, the present invention provides a novel soluble antigen, specific for Babesia parasites, isolatable from the growth medium of Babesia-infected erythrocytes in cell culture and/or from merozoite stages of the parasite in the medium. Also provided are diagnostic reagents comprising said soluble antigen.

Babesia parasites are the causative agents of hemoclastic animal diseases on a world-wide basis. Tickborne species of this genus are known to infect: cattle (*B. bovis, B. bigemina, B. divergens, B. major*); dogs (*B. canis, B. gibsoni, B. vogalia*); horses (*B. equi, B. caballi*); and rodents (*B. rodhaini, B. microti*). *B. bovis* and *B. microti* are also known to be infective in humans.

To date, no immunologically active agent has been available for use as a vaccine component in conferring immunity against infection by Babesia parasites. This is so despite very substantial attempts by those skilled in the art to isolate and purify antigenic materials by available in vivo and in vitro techniques.

Many years of research directed toward isolation of antigenic materials from the blood of infected animals have yielded a number of serum isolates displaying some attributes of antigenicity. None, however, has been successfully employed to induce a protective, much less a long-term, anamnestic, response in recipient animals. Moreover, animals innoculated with antigenic material derived from the blood of infected animals generally respond with production of iso blood group antibodies, prohibiting any practical application for such materials as vaccines. For the most part, the most successful of in vivo preparative techniques have been useful only in providing rather crude diagnostic materials.

Failures of in vitro preparative technology have been due in large part to difficulties attending quantitative, in vitro propagation of Babesia parasites, and especially to the difficulties inherent in separating suspected immunologically significant materials (e.g., killed, whole or fragmented antigenic merozoite stages of the parasite) from host erythrocyte cells and "contaminating" host cell components such as hemoglobin. Parenthetically, problems in quantitative in vitro propagation of hemotropic protozoan parasites effectively preclude development of vaccines for a wide variety of parasitic diseases including malaria (Plasmodium) and anaplasmosis (Anaplasma). Among the more pertinent recent advances in the art of parasite propagation are disclosed in Trager, et al., *Science*, 193: pp. 673–675 (1976) and Speer, et al., *Z. Parasitenk*, 50: pp. 237–244 (1976). These references, respectively, describe Plasmodium propagation in erythrocytes maintained under greatly reduced oxygen tension and continuous Plasmodium propagation in selected eukaryotic host cells. The focus of the two above-mentioned publications is the development of extracellular antigenic parasites and parasite fragments for use as vaccine components.

The general unavailability of antigenic Babesia materials has correspondingly resulted in unavailability of specific diagnostic reagents for use in determining the presence of a Babesia disease state as well as the presence of Babesia antibodies in animal serum. Presently available reagents, as noted above, generally comprise crude preparations of antigenic materials obtained from the blood of infected animals.

There exists, therefore, a substantial need in the art for antigenic Babesia materials in a substantially pure form, which materials may be used as components of vaccines and diagnostic reagents.

BRIEF SUMMARY

According to the present invention, a novel soluble Babesia antigen is isolated in quantity from the medium supporting in vitro growth of Babesia-infected erythrocytes. The antigen is characterized by: solubility in water and normal saline solutions; insolubility in from about 40% to about 70% ammonium sulfate solutions; the presence of proteinaceous and carbohydrate components; co-elution with proteins having a molecular weight on the order of about 900,000 as determined by Sephadex G-200 chromatography; heat lability; inactivation upon exposure to amylase; and susceptibility to staining with standard carbohydrate stains. The antigen is further characterized by its formation, upon counterimmunoelectrophoresis and two-dimensional immunoelectrophoresis, of at least two and three precipitin lines, respectively, with serum immunoglobulin of an animal recently recovered from Babesia infection. Finally, the soluble antigen is uniquely characterized by its ability to inhibit the capacity of specific Babesia serum antibodies to neutralize infectivity of Babesia merozoites in vitro.

Antigen preparations according to the present invention include the above-described antigen in a purified form, isolated either from the culture medium or from extracellular merozoites (themselves isolated and separated from host cellular materials by differential centrifugation). Also comprehended are antigenic preparations in the form of partially purified (e.g., by centrifugation) fractions of the total growth medium.

Vaccines according to the invention may comprise the antigen preparations in aqueous or lyophilized form and may include immunologically acceptable carriers, diluents, adjuvants and the like. Parenteral administration of the vaccines gives rise to formation of protective antibodies in the vaccinated animal within a matter of days. The protection confirmed is of the most desired type, i.e., sterile immunity. Remarkably, although antibody titers may diminish over long periods of time, vaccinated animals display an anamnestic protective response to delayed challenge by the parasite.

Purified antigen preparations may be employed according to the invention in preparation of diagnostic reagents such as antigen-sensitized particles, radiologically labeled antigen preparations and the like which are useful in conventional serodiagnostic and immunoassay techniques.

Other aspects and advantages of the invention will become apparent upon consideration of the following detailed description, wherein FIGS. 1 and 2 relate to vaccination test and challenge work involving the soluble antigen of the invention.

DETAILED DESCRIPTION

Figure 1:
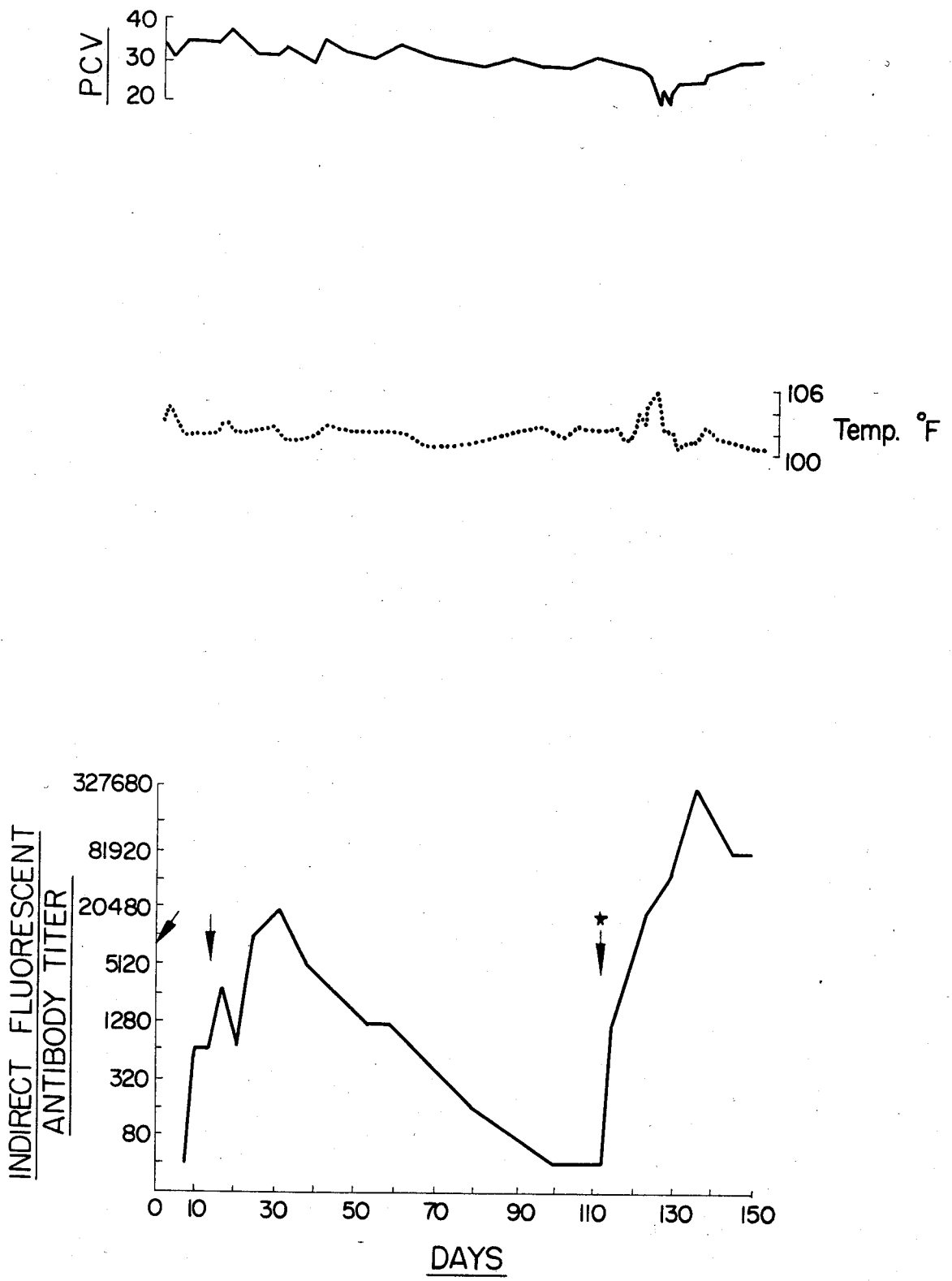

The following illustrative examples relate to presently preferred methods of practice of the invention. More specifically, the examples describe: methods for in vitro propagation of Babesia which gives rise to an antigen enriched growth medium; methods for isolation of the Babesia antigen in crude and purified forms from growth medium and from merozoites; physical and biological characterization of the novel Babesia antigen; and, demonstration of in vivo efficacy of vaccine preparations of the invention which include the antigen.

EXAMPLE 1

An antigen enriched growth medium, from which the soluble antigen of the invention is isolated, may be obtained by a modified practice of the propagative methods described in Erp, et al., *Am. Jour. Trop. Med. Hyg.*, 27 (5): pp. 1061-1064 (1978) wherein the work of the co-inventors and certain of their co-workers in successfully propagating *Babesia bovis* in bovine erythrocyte cultures is set out.

According to the procedure reported, splenectomized animals are inoculated intravenously with blood of a homologous species animal infected with a Babesia parasite. When routine microscopic examination of erythrocyte samples show that from 1 to 5 percent of the red blood cells of the inoculated animal are infected with the parasite, blood is collected and defibrinated by, e.g., shaking with glass beads. The blood is then centrifuged and the serum withdrawn and replaced with an equal volume of a mixture comprising 50 to 70 percent of a suitable medium supportive of erythrocyte growth (e.g., RPMI, MEM, or preferably Medium 199) and 30 to 50 percent serum from a non-infected heterologous species donor. Cultures so obtained are incubated at about 35°-38° C. in 100 ml spinner flasks in an atmosphere of about 5% carbon dioxide in air saturated with water vapor. Cells are kept in suspension by slow stirring with a magnetic stirrer. Subcultures are prepared, after 24-72 hours of incubation, by centrifugation of the cultures (5-10 minutes at 500×g) to collect the cells, and replacement of 50 to 70 percent of the cells with erythrocytes of a non-infected heterologous species donor, followed by resuspension in a fresh medium/serum mixture and continued incubation.

The procedures of Erp, et al., are departed from in that, rather than discarding the supernatant medium obtained during the subculturing process, the medium is saved and provides a source of the novel soluble antigen.

Alternatively, the soluble antigen of the invention may be prepared according to the much preferred methods described in U.S. patent application Ser. No. 34,663 by Miodrag Ristic and Michael G. Levy and entitled "In Vitro Parasite Propagation". (Ser. No. 130,482, filed Mar. 30, 1980). That application was filed concurrently with parent application Ser. No. 34,664.

EXAMPLE 2

Saved culture medium portions obtained according to the modified Erp, et al. method of Example 1 are pooled. Merozoite stages of parasite are isolated by 20-30 minutes of centrifuration at about 1,000×g and either discarded or saved for further processing as a source of soluble antigen. The resulting supernatant medium, having parasites and parasitic fragments removed, may be lyophilized to provide a relatively crude—but immunologically active—reddish powder suitable for use as the active agent in vaccine preparations. Alternatively, the soluble antigen may be isolated in a more purified form by selective precipitation from the medium using 40-70 percent ammonium sulfate solution. Collected precipitates are resuspended in 0.02M phosphate buffer, the pH is adjusted to 8.0 and the resulting solution is dialyzed against 0.02 phosphate buffer, pH 8.0, to yield an aqueous solution of the antigen. Lyophilization of the antigenic solution yields the purified antigen in the form of a whitish powder. In its purified, lyophilized form the antigen is substantially free of not only host erythrocyte cell fragments and cellular debris but also Babesia merozoite cell fragments and debris.

Merozoites collected in the manner noted above may be processed to yield the soluble antigen by extraction in buffered saline (pH 7.2) at 4° C. with gentle agitation to solubilize the surface coat. The resulting surface coat solution may then be purified by selective precipitation and dialysis as above to yield the antigen in pure form for use, e.g., as a vaccine component. Alternately, nonextracted (whole) lyophilized merozoites may be employed as vaccine immunogen components. Owing to possibility of infection resulting from large merozoite fragments and overall dilution of the antigen, use of such merozoite preparations in vaccines is, of course, much less preferred to use of antigen isolated from the medium.

EXAMPLE 3

The following determinations of characteristics of the soluble antigen of the invention were performed on a sample of purified (precipitated and dialyzed), lyophilized antigen of *Babesia bovis* prepared according to Example 2.

Molecular weight analysis by Sephadex G 200 chromatography showed co-elution with proteins having molecular weights on the order of 700,000 to 1,000,000.

The presence of a carbohydrate component in the antigen is verified, in part, by a staining reaction using carbofuschin.

As noted above, the antigen is soluble in water and normal saline but insoluble in 40 to 70 percent solutions of ammonium sulfate.

Specific activity of the antigen is revealed by the results of counterimmunoelectrophoresis wherein the antigen is monitored for reactivity with homologous species anti-Babesia serum obtained from a recovered animal. More specifically, the antigen forms two distinctly characteristic precipitin lines with anti-serum, which lines are observed in the following procedure. Parallel wells are cut in a 1% agarose gel overlayed on a glass plate. Immune serum is placed in the well at the anodic side (+) and the antigen is placed in the cathodic side (−). Best resolution of precipitin lines is achieved with a discontinuous buffer system in that the reservoirs contain 0.05M tris-barbitalsodium barbital buffer pH 8.8, whereas the gel contains a 0.01M solution of the same buffer. Electrophoresis is conducted at 350 V for 45 minutes at 25° C. Precipitin lines then are visualized proximal to the cathodic side of the antibody well. Specific counterimmunoelectrophoretic activity with immune serum is also observed for the "crude", lyophilized supernatant preparations (obtained as a reddish powder) according to Example 2, as well as for saline extracts of soluble antigen derived from merozoites. It should be noted that the precise electrophoretic banding characteristics described above may vary somewhat depending on such procedural factors as the constitution of the buffer and the voltage applied.

In another test, serum from rabbits immunized with *B. bovis* antigens derived from cultures which used rabbit erythrocytes and rabbit serum was reacted in a two-dimensional immunoelectrophoretic system with the supernatant fluid from positive cultures which employed bovine erythrocytes and serum. At least three antigen/antibody systems were revealed by this test. The reacting antigens showed fast mobility resembling bovine albumin. The use of normal, non-injected culture supernatant failed to demonstrate any of the above reactions.

Further evidence of a carbohydrate component of the immunologically active antigen is provided by the reduction of specific activity with immune serum when pretreated with amylase. [e.g., incubation of 100 mg of crude antigen for 16 hours at 37° C. in 0.02M buffered saline (pH 7.1) in the presence of 1 mg of alpha amylase].

As discussed in greater detail, infra, the soluble Babesia antigen is characterized by its in vivo biological activity, i.e., its ability to induce a protective response to Babesia infection. The antigen is further characterized by its unique in vitro biological activity, i.e., its ability to inhibit the capacity of specific Babesia serum antibodies to neutralize the infectivity of Babesia merozoites in vitro. The latter characteristic will be better understood upon consideration of the following examples.

EXAMPLE 4

It has been previously noted that the preferred methods for securing the antigen of the invention in quantity are set forth in co-pending U.S. patent application Ser. No. 34,663. Briefly summarized, these procedures call for propagation of Babesia parasites in erythrocytes in a medium comprising about 30 to 50 percent defibrinated serum, maintained in a controlled atmosphere having 3 to 6 percent carbon dioxide and under conditions of oxygen tension as will result in maintenance of erythrocytic hemoglobin in its deoxy state. The above procedures, referred to as microaerophilous stationary phase ("MASP") continuous cultivation procedures, are valuable not only for their capacity to produce large quantities of antigen in the growth medium but also for their capability in producing large quantities of host-cell-free merozoites (especially upon discontinuation of increased carbon dioxide tension). The extracellular merozoites are easily collected by centrifugation and stored. When supplied to cultures of erythrocytes maintained under MASP conditions, the merozoites display infectivity characteristics substantially identical to that of merozoites obtained from the blood of infected animals. The availability of infective merozoites in this essentially "concentrated" form allows for the easy determination of the presence or absence of protective antibodies in sera of animals through determination of the degree to which serum antibodies will neutralize the infectivity of merozoites.

According to such determinative procedures, MASP cultures containing uninfected erythrocytes are first allowed to incubate (for, e.g., 1 hour at 37° in a $CO_2$ incubator) with varying dilutions of test and control (normal) serum. Following incubation, 20 $\mu l$ of a cell-free merozoite suspension is added to 200 $\mu l$ of the MASP cultures contained in microtiter plates. These are allowed to incubate for from 1 to 16 hours, after which thin blood films are prepared. The percent parasitemia is determined by examination of Giemsa-stained blood films. By way of example, a 200 $\mu l$ MASP culture preincubated with 80 $\mu l$ of immune serum having an indirect fluorescent antibody "IFA" titer of 1:327,000 will completely neutralize the infectivity of 20 $\mu l$ of cell-free merozoite suspension, i.e, samples will show no parasitemia.

Modification of this merozoite neutralization ("MN") procedure provides an easy means for characterizing the soluble antigen of the invention and distinguishing it from, e.g., prior in vivo isolates. One need only ascertain whether the material possesses the ability to inhibit the ability of known of immune serum (containing specific Babesia antibodies) to neutralize infectivity of Babesia merozoites in an MN procedure such as described in the following procedure.

EXAMPLE 5

Antigen of the invention was prepared according to the MASP procedure. The specific quantity of antigen employed was that amount provided in 150 $\mu l$ of MASP culture supernatant following 3 days of in vitro culturing and wherein the average observed parasitemia had reached 16.4%. The quantity of antigen so obtained will, upon incubation with immune serum, completely inhibit the activity of 80 $\mu l$ of such serum (IFA titer 1:327,000) when the serum is thereafter employed in a merozoite neutralization procedure as described in Example 4. Dilution of this quantity of antigen by a factor of five results in an 80 percent reduction in inhibition of antibody activity, i.e., an 80 percent increase in the capacity of the antibody to neutralize the infectivity of Babesia antibodies as shown by a corresponding 80 percent drop in parasitemia.

EXAMPLE 6

In order to illustrate the absence of the above-noted characteristic in vitro activity in prior in vivo isolates, antigenic materials were prepared according to the procedures of Ristic et al. *Am. J. Vet. Res.*, 25, pp. 1519-26 (1964). Briefly summarized, a splenectomized calf was infected with the same Babesia bovis isolate employed in the MASP procedures used to make the soluble antigen tested in Example 5. An in vivo antigenic isolate was obtained from the infected animal's blood by protamine sulfate precipitation with care being taken to secure antigenic material from a number of parasites approximately equal to that involved in the MASP production of the soluble antigen of the invention. The isolate, when employed according to the procedure of Example 5, failed completley to inhibit neutralization of merozoite activity by serum antibodies.

EXAMPLE 7

The in vivo activity of vaccine preparations of the invention is demonstrated by the results obtained upon challenge of vaccinated and unvaccinated cattle with exposure to ticks (*Boophilus microplus*) infected with *Babesia bovis*. Four female holstein cattle (20 months old and weighing 500 to 1,000 pounds) were selected for study. Two animals were vaccinated with a purified, lyophilized antigen preparation of Example 2 obtained from 10 ml of supernatant from a culture having about 5 percent infected cells. This quantity of antigen was suspended in 1 ml water. Vaccinated and unvaccinated controls were all then challenged with 2000 infected tick larvae. Non-immunized cattle developed typical signs of babesiosis including anemia and hemoglobinuria. Both control animals died. Vaccinated cattle showed no clinical signs of disease although the animals were infected with *B. bovis*, as demonstrated by microscopic examination of giesma-stained thin blood smears. Vaccinated cattle were long term survivors.

EXAMPLE 8

Vaccine materials containing both corpuscular and soluble antigen fractions prepared according to the modified Erp, et al. procedure of Example 2 were employed in a field study as reported in Smith, et al., *Am. J. Vet. Res.*, 40, pp. 1678–1682 (1979). The degree afforded by the vaccines, which employed Freund's Complete and Incomplete Adjuvants, was less dramatic in the field study than in the previous Example 7, possibly due to defects in the collection, isolation and purification of antigen from the culture medium and perhaps due to the adjuvant employed.

EXAMPLE 9

Figure 2:
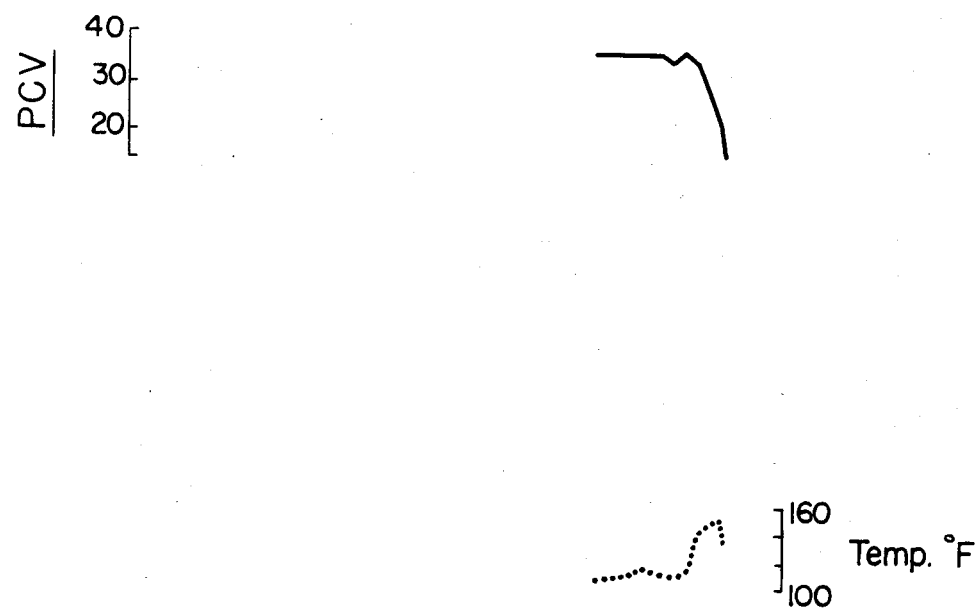
Figure 2:
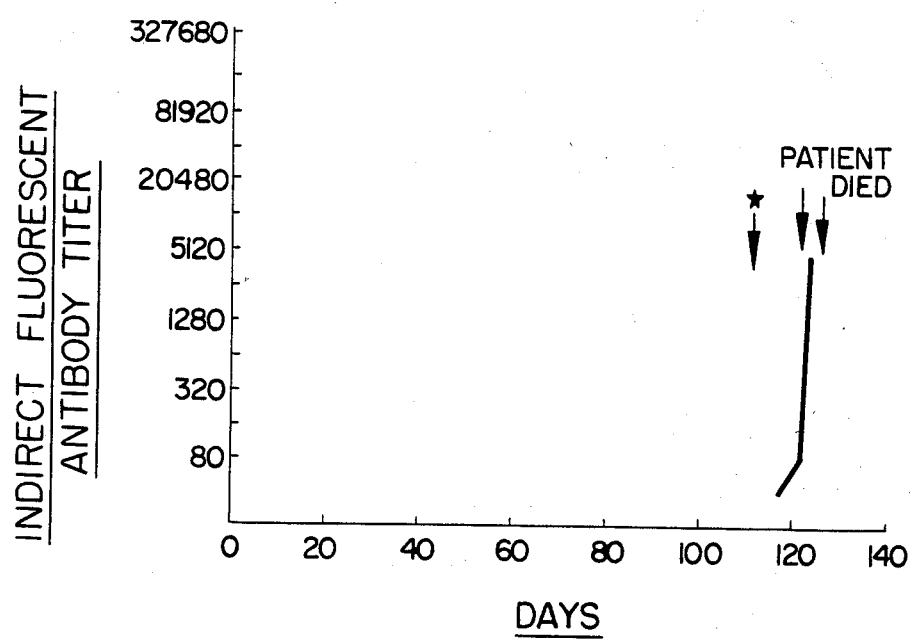

FIGS. 1 and 2 illustrate in part the results of a further test of the in vivo biological activity characteristic of the soluble antigen of the invention. A vaccine was prepared from MASP culture supernatant. Each dose contained the lyophilized soluble antigen fraction isolated from 10 ml of MASP culture supernatant (wherein the average parasitemia following 3 days of in vitro propagation was about 16.4 percent) reconstituted with 1 ml water and 1 ml of saponin adjuvant (Quil-A). Two adult Holstein cows were used in the study and monitored for variations in Babesia serum antibodies (expressed as IFA titer), variations in rectal temperatures (expressed in °F.) and variations in packed cell volume of blood (expressed as a percentage of total blood volume). FIG. 1 provides data for the experimental animal and FIG. 2 provides data for the control animal. The experimental cow was injected with a first dose of the vaccine on day 0 and a second dose on day 14 (noted by the unstarred arrows in FIG. 1). Antibody titers for the experimental animal rose to a peak at about day 35 and then gradually diminished. Temperature and packed cell volume data remained relatively constant. At day 112, both the experimental and control animals were challenged by intramuscular injection of $1 \times 10^8$ virulent *Babesia bovis* (noted by the starred arrows in FIGS. 1 and 2). Antibody titers rose precipitously in the experimental animal almost immediately, indicating a true anamnestic immune response. While body temperature rose, it returned to normal in a few days. Similarly, packed cell volume diminished somewhat but soon returned to normal ranges. The control animal, on the other hand, showed no antibody development until nearly ten days following challenge at which time parasites were patent in blood smears, temperature had risen steadily and packed cell volume had dropped precipitously. On day 124 the control animal died. The vaccinated experimental animal was a long term survivor.

EXAMPLE 10

The sterile immunity characteristics derived by the practice of vaccination methods of the invention are illustrated by the absence of infectivity of blood of vaccinated animals. More particularly, for example, 50 ml of blood of the experimental animal of Example 9 was withdrawn 28 days after challenge (i.e., about day 140) and injected into the circulatory system of a splenectomized calf. The calf failed to become infected even though it was later shown to be susceptible to infection by challenge with *Babesia bovis*.

While not intended to be binding on the scope of the present invention, the following remarks may serve to explain in part the basis for its physical and biological properties vis-a-vis prior antigenic Babesia materials. It has been found that the soluble antigen of the invention may be obtained in quantity from an in vitro growth medium wherein merozoites are essentially constantly being formed and are constantly infecting erythrocytes. The antigen is also available by a rather gentle washing of the surfaces of such in vitro-propagated merozoites. These two facts lend substantial support to the propositions that: (1) the soluble antigen has its origins as a loosely-bound surface component of infective Babesia merozoites; and (2) the soluble antigen, after serving a "host recognition" function, is "shed" by the merozoite in the process of invading an erythrocyte.

Within the context of such a model of events surrounding the infection process, the physical and biological characteristics of the soluble antigen may be understood. If the antigen, when associated with the surface of a merozoite, serves to allow recognition of a proper host cell by the merozoite, it is likely that this non-infective substance alone would itself be "recognized" by the immune system of a vaccinated animal and give rise to protective antibody production without involvement of an infectious process. This model also serves to explain similarities and differences between the antigen of the present invention and prior in vivo isolates. If antigenic material is transitorily associated with and shed by merozoites upon invasion of erythrocytes, it would expectedly be available in at least small quantities from infected animal serum. Indeed, some of the prior in vivo isolates are reported to include protein and non-protein components somewhat similar to those possessed by the soluble antigen of the invention. Others display similar solubility properties in ammonium sulfate solutions. That none share the in vivo and in vitro biological activity of the antigen of the invention may be attributable to a rapid degradation of "active" elements within the host's circulatory system, so that prior antigenic isolates may in fact comprise only fragments of their prior total and active constitution. It is certainly understandable that such antigenic "artifacts" would not display the biological activity needed for, e.g., an operative protective vaccine.

It is expected that as a result of the present invention, many studies will be directed toward characterization of "active site(s)", if any, within the soluble antigen. Such studies, made possible by the availability for the first time of a truly immunologically active substance in quantity, are likely to lead to the future chemical or biological synthesis of perhaps drastically simpler, but nonetheless active, antigenic substances. While such chemically or biologically synthesized materials might no longer share the physical characteristics of the antigen of the invention in terms of molecular weight, ammonium sulfate solution solubility, or even protein/carbohydrate constituents would necessarily share the in vivo and in vitro biological characteristics noted above.

The specific Babesia antigens of the invention may be used to sensitize immunologically inert particles of varying types well known in the art as useful in diagnostic, antigen-antibody reaction detection schemes. In this regard, antigen preparations and antigen-sensitized particles of the invention may be used in combination with suitable "marker" substances (chemical and radiochemical) in the detection of antibodies by agglutination, radioimmunoassay, as well as fluorescent and enzyme immunoassay techniques.

As noted above, although not particularly preferred, vaccine preparations of the invention may comprise the novel antigen in the form of crude or purified culture medium or merozoite isolates. When the preferred, precipitation and dialysis purified antigen (in lyophilized, whitish powdery form) is employed, a dosage amount of from 0.5 to 5.0 mg per adult animal is suitable for protecting animals susceptible to Babesia infection. A variety of immunologically acceptable carriers, diluents and adjuvants (such as Quil-A and Fruend's Incomplete Adjuvant, with the former detergent-type adjuvant being preferred) may be employed in formulating vaccines according to the invention.

Numerous modifications and variations of the above-described invention are expected to occur to those skilled in the art and consequently only such limitations as appear in the appended claims should be placed thereon.

What is claimed:

1. A water soluble antigen, specific for Babesia parasites, produced in vitro and characterized by the ability to inhibit the capacity of specific Babesia serum antibodies to neutralize the infectivity of Babesia merozoites in vitro.

2. An antigen according to claim 1 and further chacraceteized by the ability to induce, in vivo, formation of antibodies protective against infection by Babesia parasites.

3. An antigen according to claim 1 and specific for Babesia parasite species selected from the group consisting of *B. bovis, B. bigemina, B. divergens, B. major, B. canis, B. gibsoni, B. vogali, B. equi, B. caballi, B. rodhaini* and *B. microti.*

4. An antigen according to claim 3 specific for *Babesia bovis* species parasites.

5. An antigen according to claim 1 and further characterized by having proteinaceous and carbohydrate constituents, by being insoluble in 40 to 70 percent ammonium sulfate solution, and by forming two distinct counterimmunoelectrophoretic and three distinct two-dimensional immunoelectrophoretic precipitation bands with serum reactive with Babesia parasites.

6. A vaccine for use in conferring protection upon an animal against infection by a Babesia parasite, said vaccine comprising in unit dosage form:
   an immunologically effective amount of a water soluble antigen, specific for Babesia parasite, produced in vitro and characterized by the ability to inhibit the capacity of specific Babesia serum antibodies to neutralize the infectivity of Babesia merozoites in vitro; and
   an immunologically acceptable diluent, adjuvant or carrier.

7. A vaccine according to claim 6 wherein said soluble antigen is specific for Babesia parasite species selected from the group consisting of *B. bovis, B. bigemina, B. divergens, B. major, B. canis, B. gibsoni, B. vogali, B. equi, B. caballi, B. rodhaini* and *B. microti.*

8. A vaccine according to claim 7 wherein said soluble antigen is specific for *Babesia bovis* species parasites.

9. A vaccine according to claim 6 wherein said soluble antigen is further characterized by having proteinaceous and carbohydrate constituents, by being insoluble in 40 to 70 percent ammonium sulfate solution, and by forming two distinct counterimmunoelectrophoretic and three distinct two-dimensional immunoelectrophoretic precipitation bands with serum ractive with Babesia parasites.

10. A diagnostic reagent for use in detection of a babesiosis disease state, said reagent comprising:
    a water soluble antigen, specific for a Babesia parasite, produced in vitro and characterized by the ability to inhibit the capacity of specific Babesia serum antibodies to neutralize the infectivity of Babesia merozoites in vitro; and
    an immunologically acceptable carrier or marker substance.

* * * * *